United States Patent
Ooida et al.

(10) Patent No.: US 8,225,781 B2
(45) Date of Patent: Jul. 24, 2012

(54) INHALATION APPARATUS

(75) Inventors: Junichi Ooida, Tokyo (JP); Takahiro Hatanaka, Kawasaki (JP); Katsuhiko Shinjo, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 1284 days.

(21) Appl. No.: 11/872,361

(22) Filed: Oct. 15, 2007

(65) Prior Publication Data
US 2008/0092880 A1    Apr. 24, 2008

(30) Foreign Application Priority Data

Oct. 18, 2006  (JP) .................................. 2006-283221

(51) Int. Cl.
*A61M 11/00* (2006.01)

(52) U.S. Cl. ......... 128/200.24; 128/201.13; 128/205.12; 128/205.27

(58) Field of Classification Search ............. 128/200.24, 128/201.13, 203.12, 203.15, 205.12, 205.25–205.29, 128/206.17, 206.22; 261/DIG. 65
See application file for complete search history.

(56) References Cited

U.S. PATENT DOCUMENTS

| | | | | |
|---|---|---|---|---|
| 3,695,267 A * | 10/1972 | Hirtz et al. | ............... | 128/203.17 |
| 4,367,734 A * | 1/1983 | Benthin | ................... | 128/204.13 |
| 5,255,674 A * | 10/1993 | Oftedal et al. | ........... | 128/203.16 |
| 6,367,472 B1 * | 4/2002 | Koch | ........................ | 128/203.12 |
| 6,415,788 B1 * | 7/2002 | Clawson et al. | ......... | 128/201.13 |
| 6,557,551 B2 * | 5/2003 | Nitta | ......................... | 128/203.17 |
| 6,679,250 B2 * | 1/2004 | Walker et al. | ............ | 128/200.21 |

FOREIGN PATENT DOCUMENTS

| | | |
|---|---|---|
| WO | 95/01137 A1 | 1/1995 |
| WO | 96/09846 A1 | 4/1996 |
| WO | 02/04043 A2 | 1/2002 |

* cited by examiner

*Primary Examiner* — Steven Douglas
(74) *Attorney, Agent, or Firm* — Fitzpatrick, Cella, Harper & Scinto

(57) ABSTRACT

In order to control the amount of evaporation of discharged agent droplets and so that a user can inhale agent droplets having a constant diameter regardless of use environment, an inhalation apparatus includes an airflow path communicating with a suction port through which the user inhales an agent, an agent discharging portion configured to discharge an agent supplied to the airflow path, and a humidifier located outside the airflow path and configured to humidify an airflow in the airflow path generated by an inhalation of the user.

10 Claims, 10 Drawing Sheets

FIG. 8

FIG. 9

INHALATION APPARATUS

BACKGROUND OF THE INVENTION

1. Field of the Invention

The present invention relates to an inhalation apparatus that discharges an agent such as medicine, fragrance, or nicotine so that the user can inhale it.

2. Description of the Related Art

A method for dosing using an inhalation apparatus is known. Unlike an injection, such dosing through the respiratory system does not cause pain. Such an inhalation apparatus can also serve as a portable terminal including a storage unit that stores information on the user including the user's medical record and prescription, and a discharge device that discharges an agent in the form of minute droplets so that the user can inhale them. Such an inhalation apparatus can also include a discharge control unit that makes the discharge device discharge the agent according to the user's inhalation profile so that the user can inhale the agent according to the prescription information (see WO95/01137 and WO02/04043).

In inhalation apparatuses, it is necessary to accurately control the dose of the agent. The diameter of agent droplets is important to accurately control the dose. The diameter of agent droplets at the suction port through which the user inhales affects the amount of agent that reaches the user's lungs. That is, if the amount of agent discharged from an inhalation apparatus is constant but the diameter of agent droplets is larger or smaller than the optimum value, the amount of agent that the user can inhale decreases. Specifically, droplets having a diameter of around 3 µm can reach the user's alveoli. Droplets having a diameter larger than around 3 µm cannot reach the user's alveoli and are deposited in the user's bronchi, for example. It is known that droplets having a diameter smaller than around 3 µm are not absorbed into the user's body and are discharged by exhalation. However, in the case where an agent is discharged in the form of minute droplets, the diameter of droplets changes due to evaporation.

The amount of evaporation fluctuates with changes in the surrounding environment, for example, factors such as temperature and humidity. Therefore, it is difficult to keep the diameter of agent droplets at the optimum value. As a result, the amount of agent that the user inhales cannot be accurately controlled. Therefore, an inhalation apparatus in which a constant droplet diameter can be obtained regardless of use environment is desirable.

As a solution to this problem, WO96/009846 discloses an inhaler that functions to accelerate evaporation using a heater and a dehumidifier so as to make the droplet diameter constant. This document also describes saturating inhaled air with water vapor so as to prevent evaporation of droplets.

However, the configuration disclosed in the above document requires a heater or a dehumidifier that accelerates evaporation to control the change in droplet diameter due to evaporation. Located inside the airflow path, it can interfere with the inhalation airflow and therefore can interfere with ease of inhalation of the user. There is no description of a specific water-vapor generator, including the position where the generator is located.

In the case where the discharged agent does not spread throughout the airflow path, it is not necessary to make the entire airflow path an evaporation-controlled environment. This leads to wasteful consumption of energy in the inhalation apparatus and an increase in weight and size of the inhalation apparatus, and consequently degrades the portability of the inhalation apparatus.

SUMMARY OF THE INVENTION

The present invention is directed to a highly portable inhalation apparatus that can keep the diameter of inhaled agent droplets constant regardless of use environment and can efficiently dose the user.

In an aspect of the present invention, an inhalation apparatus includes an airflow path communicating with a suction port through which a user inhales an agent, an agent discharging portion configured to discharge an agent supplied to the airflow path, and a humidifier located outside the airflow path and configured to humidify an airflow in the airflow path generated by an inhalation of the user.

The inhalation apparatus of the present invention can restrain the evaporation of agent droplets discharged from the agent discharger, by humidifying an airflow (inhaled air) generated by an inhalation of the user. Therefore, the user can inhale agent droplets having a constant diameter regardless of use environment.

Since the humidifier is located outside the airflow path, the humidifier does not interfere with inhalation of the user.

Further features of the present invention will become apparent from the following description of exemplary embodiments with reference to the attached drawings.

BRIEF DESCRIPTION OF THE DRAWINGS

FIG. 1 is a perspective view showing outer appearance of an example of an inhalation apparatus of the present invention.

FIG. 2 is a schematic sectional view showing the inside of the apparatus of FIG. 1.

FIG. 3 is a schematic sectional view showing the inside of an inhalation apparatus according to a second embodiment.

FIG. 4 is a schematic sectional view showing the inside of an inhalation apparatus according to a third embodiment.

FIG. 5 is a schematic sectional view showing the inside of an inhalation apparatus according to a fourth embodiment.

FIG. 6 is a schematic sectional view showing the inside of an inhalation apparatus according to a fifth embodiment.

FIG. 7 shows a modification of the fifth embodiment.

FIG. 8 illustrates the operation of the apparatus of FIG. 6.

FIG. 9 is a timing diagram showing the operation of the apparatus of FIG. 6.

FIG. 10 is a schematic view showing the principal part of an inhalation apparatus according to a sixth embodiment.

FIG. 11 shows a modification of the sixth embodiment.

FIG. 12 is a schematic view showing the principal part of an inhalation apparatus according to a seventh embodiment.

FIG. 13 is a block diagram showing a control system of an inhalation apparatus of the present invention.

DESCRIPTION OF THE EMBODIMENTS

Embodiments of the present invention will now be described in detail in accordance with the accompanying drawings.

First, the basic structure of an inhalation apparatus of the present invention will be described with reference to FIG. 1.

FIG. 1 is a perspective view showing outer appearance of an example of an inhalation apparatus of the present invention. The inhalation apparatus includes a housing and a mouthpiece 4. The housing includes an inhalation apparatus main body 1, an access cover 2, and a front cover 3. The inhalation apparatus main body 1 has a power button 1*a*. The mouthpiece 4 has a suction port through which the user inhales an agent. A hook provided at an end of a locking lever 5 and urged by a spring engages with a protrusion provided at an end of the access cover 2 so that the access cover 2 does not open when the apparatus is used.

When the locking lever 5 is slid downward, the access cover 2 rotates around a hinge shaft (not shown) so as to open by the force of an access-cover returning spring (not shown) that urges the access cover 2.

Figure 1:
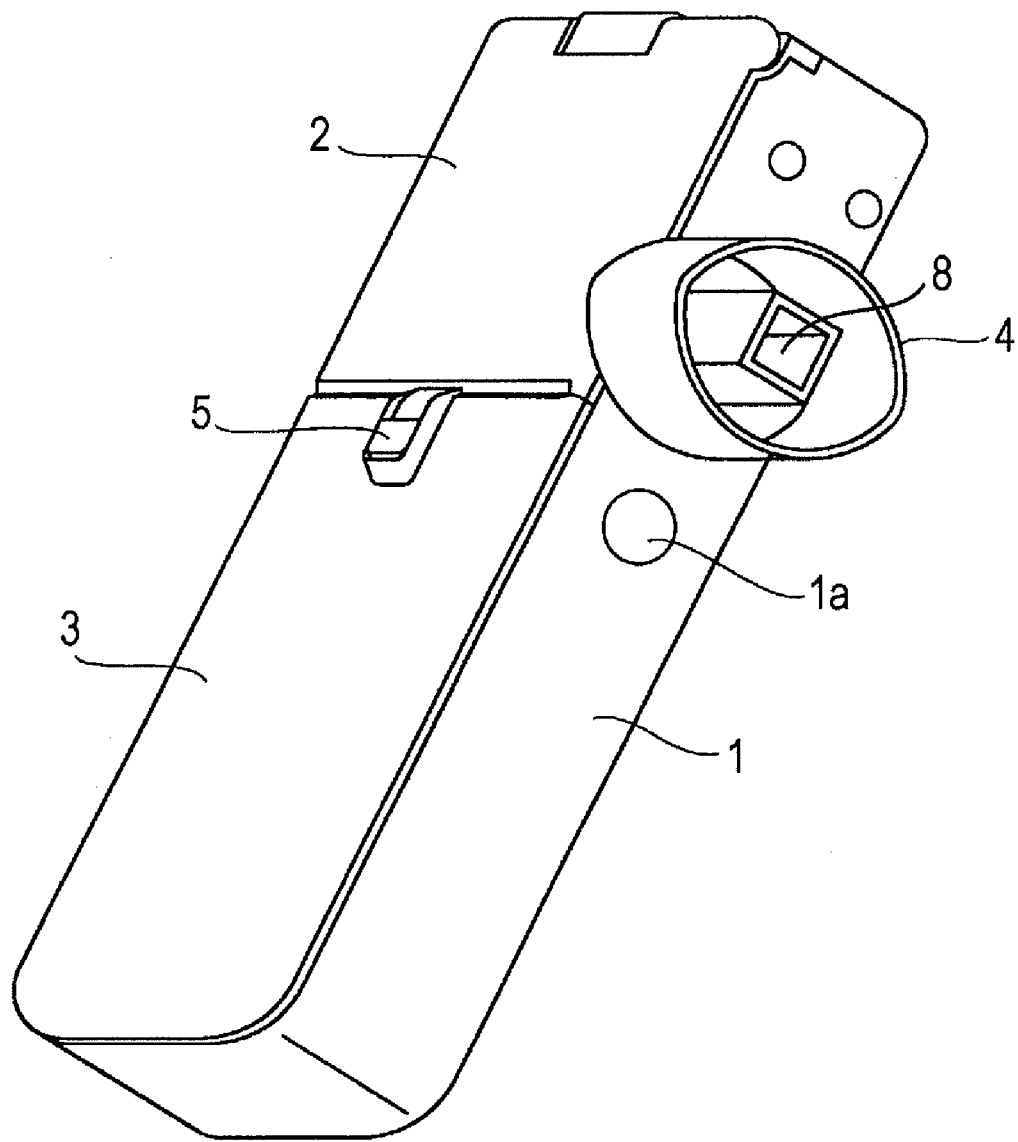
Figure 2:
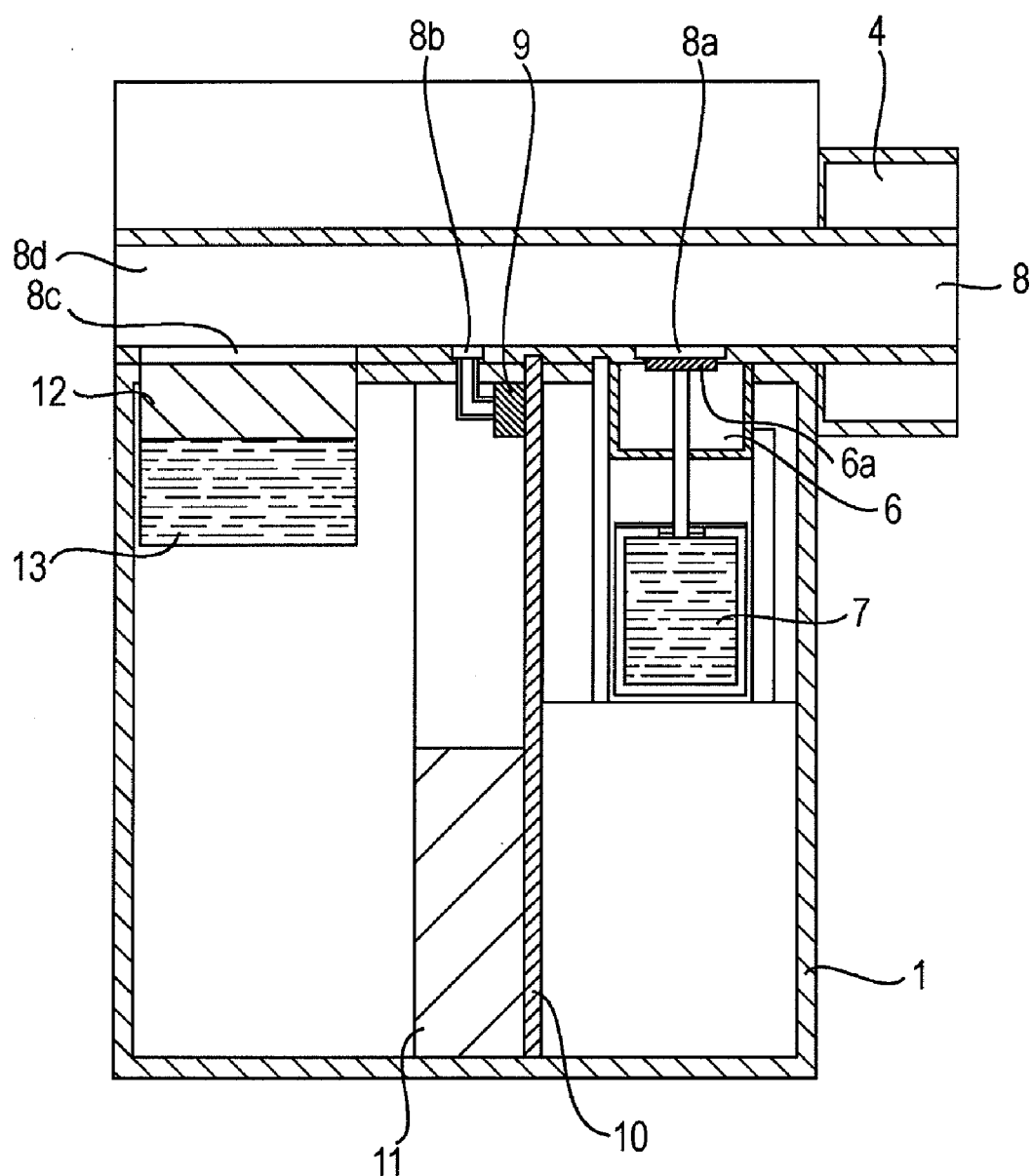

FIG. 2 is a sectional view showing the inhalation apparatus with the access cover 2 open and an agent discharge cartridge 6 and a reservoir 7 loaded in the inhalation apparatus main body 1. The agent discharge cartridge 6 includes an agent discharge head 6a serving as an agent discharger. The reservoir 7 is a tank that holds agent liquid (an agent) to be discharged from the agent discharge cartridge 6. The reservoir 7 communicates with the agent discharge cartridge 6. The discharge head 6a included in the agent discharge cartridge 6 is located at the position of an opening 8a of an airflow path 8. The discharge head 6a discharges the agent into the airflow path 8. Thus, the agent discharged from the discharge head 6a is supplied to the airflow path 8. One end of the airflow path 8 communicates with the mouthpiece 4, and the other end is an air intake 8d. The user holds the mouthpiece 4 in their mouth and inhales. An airflow is thereby generated in the airflow path 8. The agent discharged from the discharge head 6a is carried by the airflow and enters the user's body.

The reservoir and the discharge head may be integrated so as to form a cartridge.

The term "agent" used in the present invention includes not only pharmaceutical compounds having pharmacological and physiological properties but also seasoning and flavoring components, fragrances, dyes, and pigments. In this specification, agent liquid (an agent in the form of liquid or a solution containing an agent) will be sometimes referred to as "agent." The agent liquid may contain any additives. The state of the agent in the liquid may be any one of dissolution, dispersion, emulsion, suspension, and slurry. The agent can be homogenized in the liquid.

In the present invention, the principle of discharge by the agent discharger (discharge head) is not limited as long as it can atomize the agent liquid. The agent discharger has a given discharge-energy generating element, for example, an electro-thermal conversion element that imparts thermal energy to the agent liquid, or an electromechanical conversion elements that imparts mechanical energy. That is, as examples of methods for discharging agent liquid, there can be mentioned a method (thermal jet method) in which thermal energy is imparted to agent liquid using an electro-thermal conversion element so that the agent liquid can be discharge and a method in which agent liquid is discharged using vibratory pressure of an electromechanical conversion element (e.g., piezoelectric element) that imparts mechanical energy to the agent liquid. The discharge method to be used is selectable according to the kind of agent liquid, for example.

In the case where the thermal jet method is used, the accuracy of the diameter of the discharge port, the amount of heat of the thermal pulse used for discharge, and the size of a micro-heater, for example, serving as an electro-thermal conversion element, and the reproducibility can be increased with respect to each agent cartridge. Therefore, a narrow droplet diameter distribution can be achieved. In addition, the production cost of the head is low, and therefore the applicability to small apparatuses that require frequent head replacement is high. Therefore, a thermal jet discharge device is suitable particularly for apparatuses requiring portability and user-friendliness, such as inhalation apparatuses.

A pressure sensor 9 serves as an inhalation detecting unit for detecting the user's inhalation and efficiently discharging the agent in synchronization with the inhalation. The pressure sensor 9 is placed on a control board 10 including a CPU that controls the operation of the inhalation apparatus. Since the pressure sensor 9 communicates with the pressure detection port 8b communicating with the airflow path 8, the pressure sensor 9 can detect negative pressure generated in the airflow path 8 by the user's inhalation. The inhalation apparatus main body 1 has a built-in battery 11 so that the user can carry the inhalation apparatus and use it anywhere.

The inhalation apparatus of the present invention is characterized in that a humidifier for humidifying an airflow generated by the user's inhalation is located outside the airflow path 8. If the humidifier is located inside the airflow path 8, the humidifier interferes with the airflow generated by the user's inhalation, and a turbulent flow can be generated in the airflow. This is undesirable for inhalation of agent droplets. If the humidifier is located outside the airflow path 8, it is possible to humidify the airflow without generating a turbulent flow in the airflow. The specific embodiments will hereinafter be described.

First Embodiment

A first embodiment will be described with reference to FIG. 2. In the inhalation apparatus according to this embodiment, a porous body 12 is located upstream of the discharge head 6a in the inhalation airflow in the airflow path 8. The porous body 12 serves as a liquid holder and a humidifier that supplies moisture for humidifying the airflow generated by the use's inhalation. The porous body 12 communicates with the liquid tank 13. By tilting the inhalation apparatus, liquid is supplied to the porous body 12. The water held in the porous body 12 evaporates, thereby generating water vapor. This water vapor flows into the airflow path 8 through a humidification port 8c, thereby humidifying the inhalation airflow.

The porous body 12 is formed of a material capable of holding water, for example, a sponge.

A film that transmits vapor but does not transmit water can be placed at the humidification port 8c so that water does not leak into the airflow path 8.

The user may supply the liquid tank 13 with water themselves. Alternatively, the liquid tank 13 may hold water and be hermetically sealed. In this case, the user removes a cover at the time of humidification. The liquid tank 13 may be detachable together with the porous body 12. In this case, the liquid tank 13 can be replaced together with the porous body 12. Due to these, the user can inhale agent droplets having a constant diameter regardless of use environment.

In this specification, the term "detachable" includes the case where the humidifier is screwed to the inhalation apparatus. The humidifier can be attached so that the user can detach it easily, for example, by just pulling. The humidifier can be attached and detached by sliding.

Second Embodiment

Figure 3:
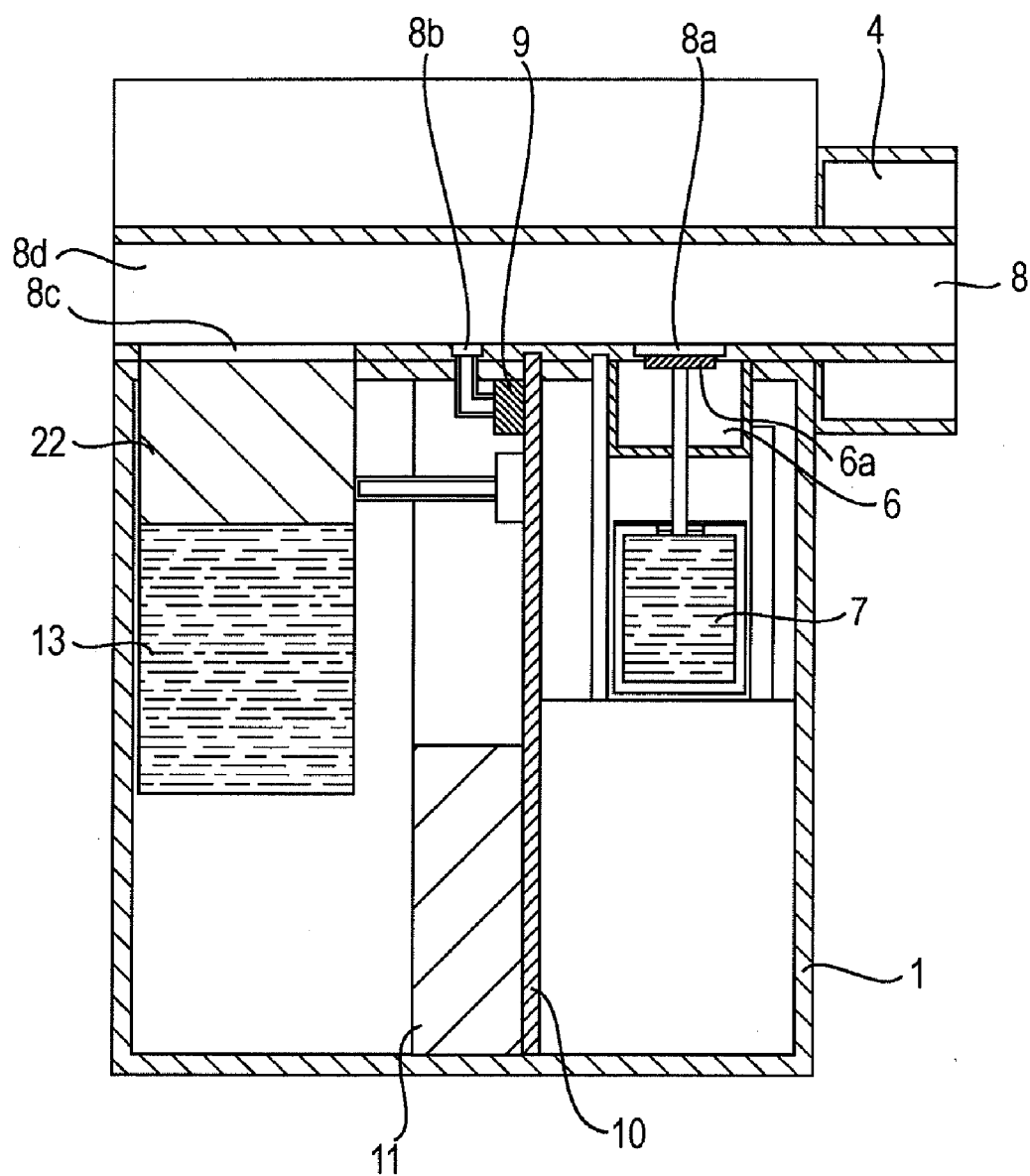
Figure 4:
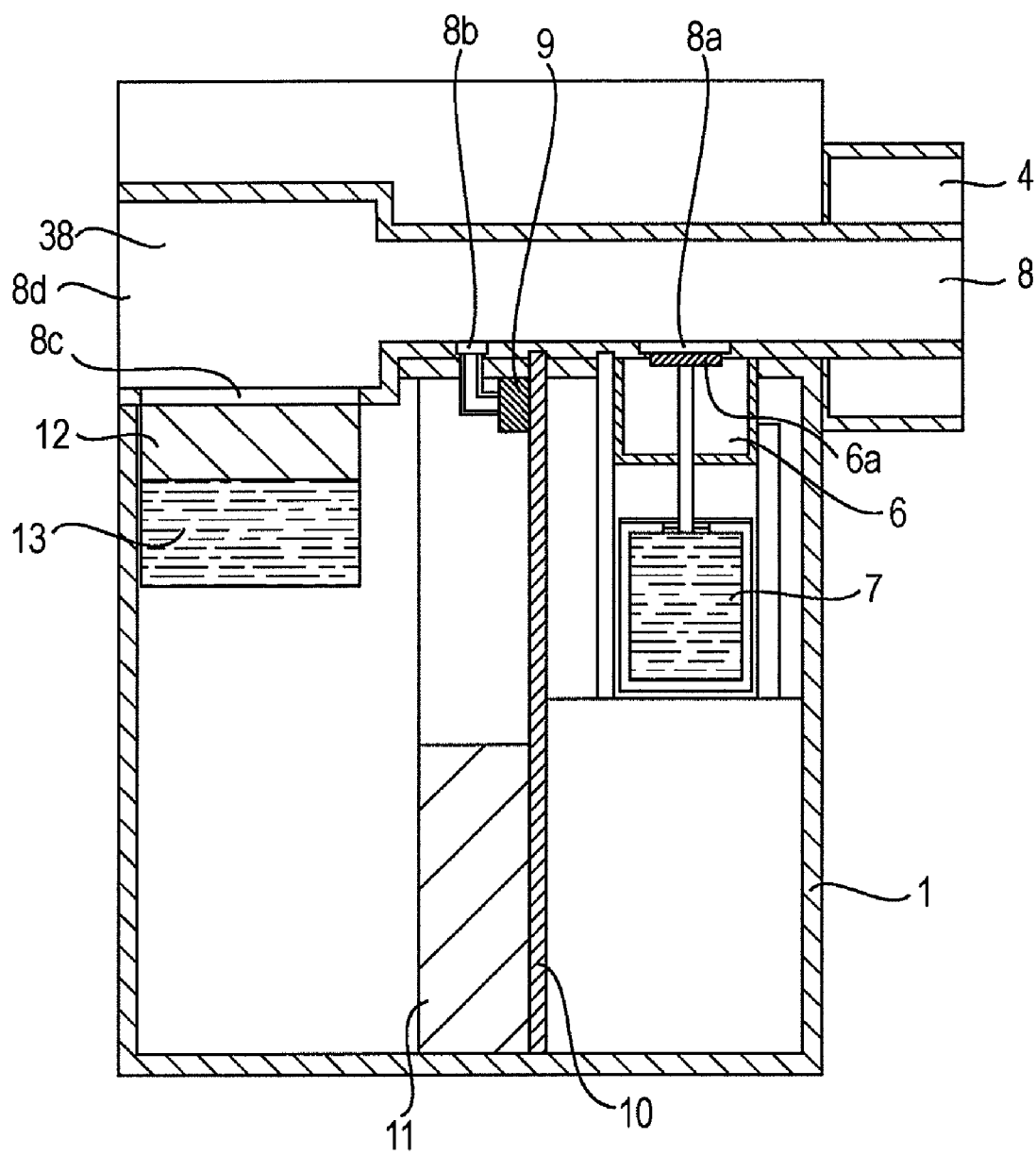

FIG. 3 is a sectional view of an inhalation apparatus according to a second embodiment. This embodiment differs from the first embodiment in that it uses a nebulizer 22 that discharges mist such as water vapor. The nebulizer 22 is supplied with water from a liquid tank 13 communicating therewith. The nebulizer 22 is controlled by a control board 10 and can include a heater so that water vapor can be easily generated. The nebulizer 22 can discharge not only water vapor but also another gas or liquid into the airflow path 8. For example, the nebulizer 22 can discharge flavored gas together with water vapor so that the user can inhale easily.

Third Embodiment

FIG. 4 is a sectional view of an inhalation apparatus according to a third embodiment. This embodiment differs from the first embodiment in that an enlarged flow path 38 having an enlarged cross-sectional area is formed at the position where the humidification port 8c of the airflow path 8 is located. That is, the cross-sectional area of a part of the airflow path where the humidifier is located is larger than the cross-sectional area of a part of the airflow path where the discharge head 6a is located. In the case where this method is used, the flow velocity in the enlarged flow path part is smaller. Therefore, inhaled air is humidified more efficiently.

Fourth Embodiment

Figure 5:
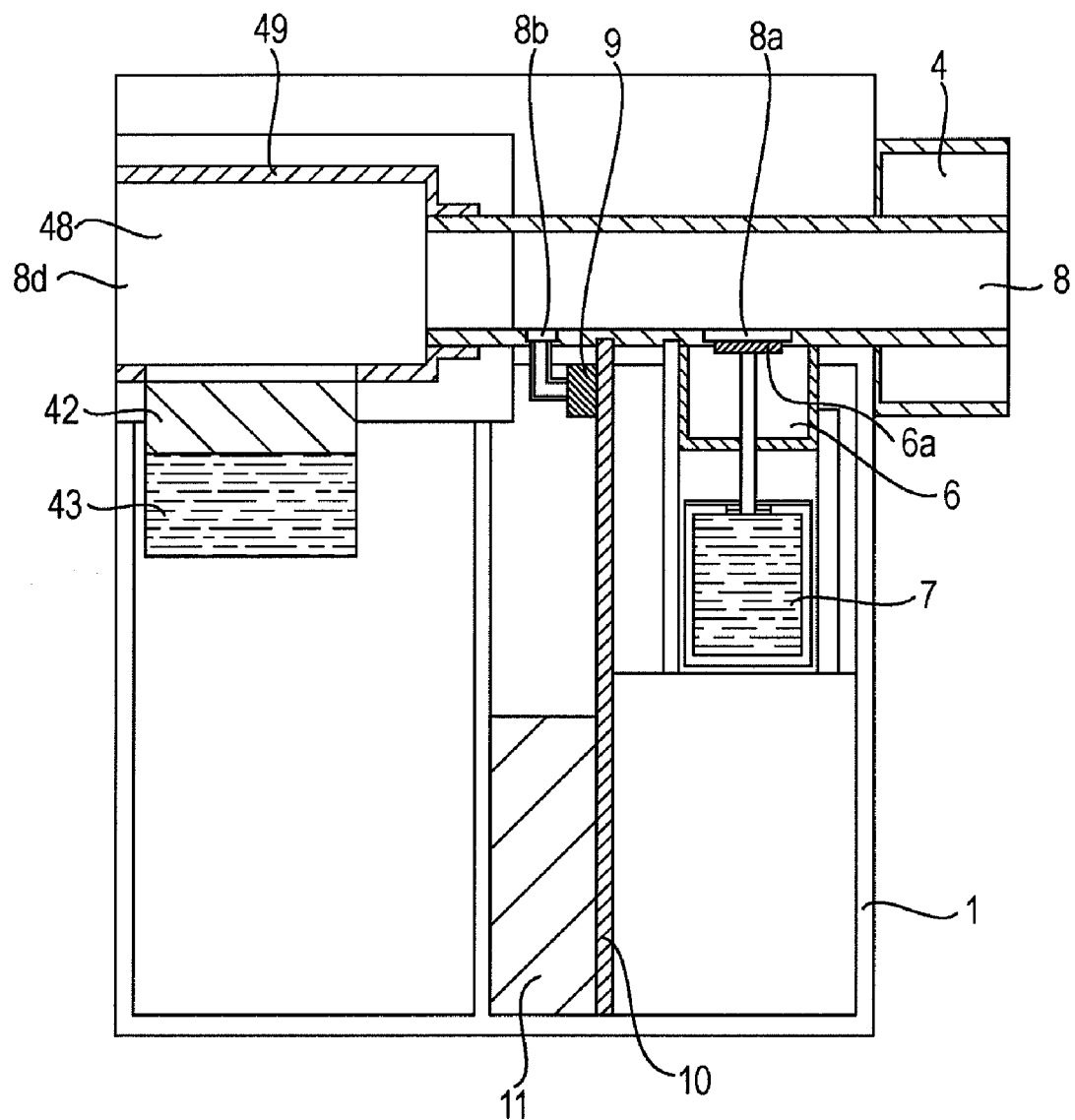

FIG. 5 is a sectional view of an inhalation apparatus according to a fourth embodiment. In this embodiment, an enlarged flow path 48 is formed on the air intake 8d side of the airflow path 8, and a humidifier 49 including a porous liquid holding member 42 and a liquid tank 43 is integrated with the enlarged flow path 48 and can be detached and replaced together therewith. That is, the humidifier can be replaced together with a part of the airflow path. This replaceable humidifier 49 is replaced according to at least one of the humidity and temperature around the user, the droplet diameter of discharged agent, the composition of discharged agent droplets, the temperature of discharged agent droplets, the discharge velocity, the discharge frequency, the discharge time, and the airflow velocity. By changing the relative positional relationship between the humidifier 49 and the discharge head 6a, the amount of humidification, the cross-sectional area of the enlarged flow path 48, and so forth, more efficient humidification can be achieved.

Instead of replacing the humidifier 49, it is possible to electrically control, for example, a motor and thereby automatically change at least one of the relative positional relationship between the humidifier 49 and the discharge head 6a, the amount of humidification, and the cross-sectional area of the enlarged flow path 48.

Fifth Embodiment

Figure 6:
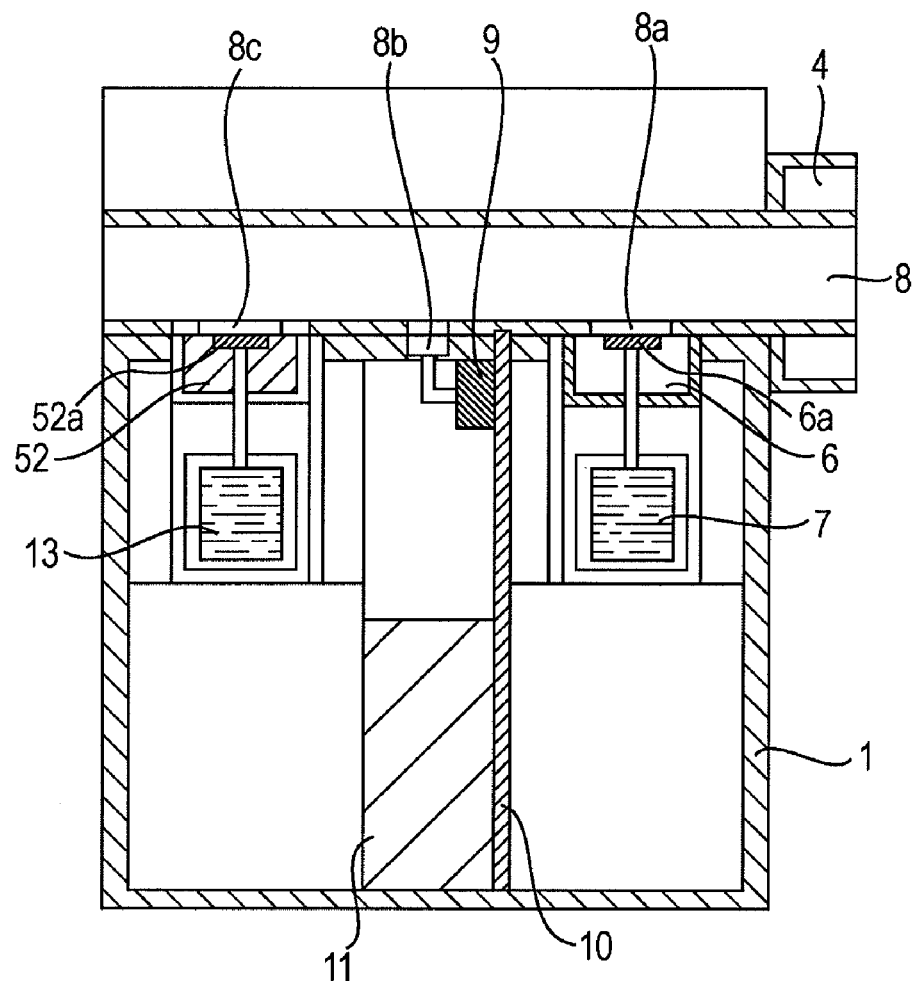

FIG. 6 is a sectional view of an inhalation apparatus according to a fifth embodiment. Instead of the porous liquid holding member 12 in the first embodiment, this embodiment has a humidifying droplet discharge unit 52 that communicates with a liquid tank 13 containing humidifying liquid. The liquid tank 13 communicates with the humidifying droplet discharge unit 52. The humidifying droplet discharge unit 52 includes a discharge head 52a serving as a humidifying liquid discharger. The humidifying droplets discharged from the discharge head 52a flow into the airflow path 8 through the humidification port 8c. As a result, the air inhaled by the user is humidified, and the evaporation of agent droplets can be prevented.

The structure of the discharge head 52a serving as a humidifying liquid discharger can be the same as the structure of the discharge head 6a discharging agent liquid to be inhaled. The CPU included in the control board 10 also functions as a discharge control unit controlling the discharge head 52a.

A pressure sensor 9 is placed on the control board 10. The pressure sensor 9 serves as an inhalation detecting unit for detecting the user's inhalation and efficiently discharging agent droplets and humidifying droplets in synchronization with the inhalation. The control board 10 includes the CPU. The CPU is a discharge control unit that controls the discharging operation.

In order to prevent the evaporation of agent droplets, the humidifying droplet discharge unit 52 can be located upstream of the agent discharge cartridge 6. By locating the humidifying droplet discharge unit 52 upstream of the agent discharge cartridge 6, the air inhaled by the user is humidified, and the evaporation of agent droplets is prevented.

By making the diameter of humidifying droplets smaller than that of agent droplets, the time for the air inhaled by the user to be saturated can be shortened. That is, it is desirable to discharge humidifying droplets smaller than agent droplets. Specifically, the diameter of the discharge port (nozzle) of the discharge head 52a that discharges humidifying liquid is smaller than the diameter of the discharge port (nozzle) of the discharge head 6a that discharges agent liquid.

Figure 7:
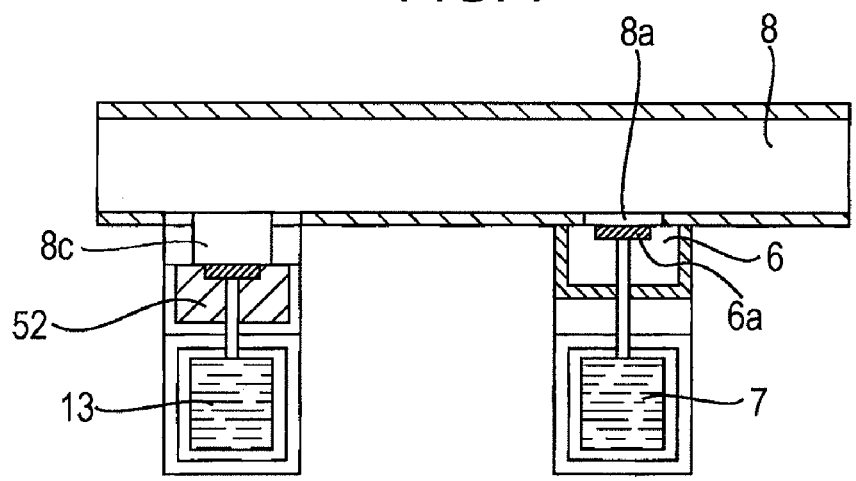

As shown in FIG. 7, the humidifying droplet discharge unit 52 may be located away from the humidification port 8c. In this case, the amount of discharged humidifying droplets may be changed according to the environmental humidity, for example. Specifically, the number of humidifying droplets may be changed.

Figures 8, 9:
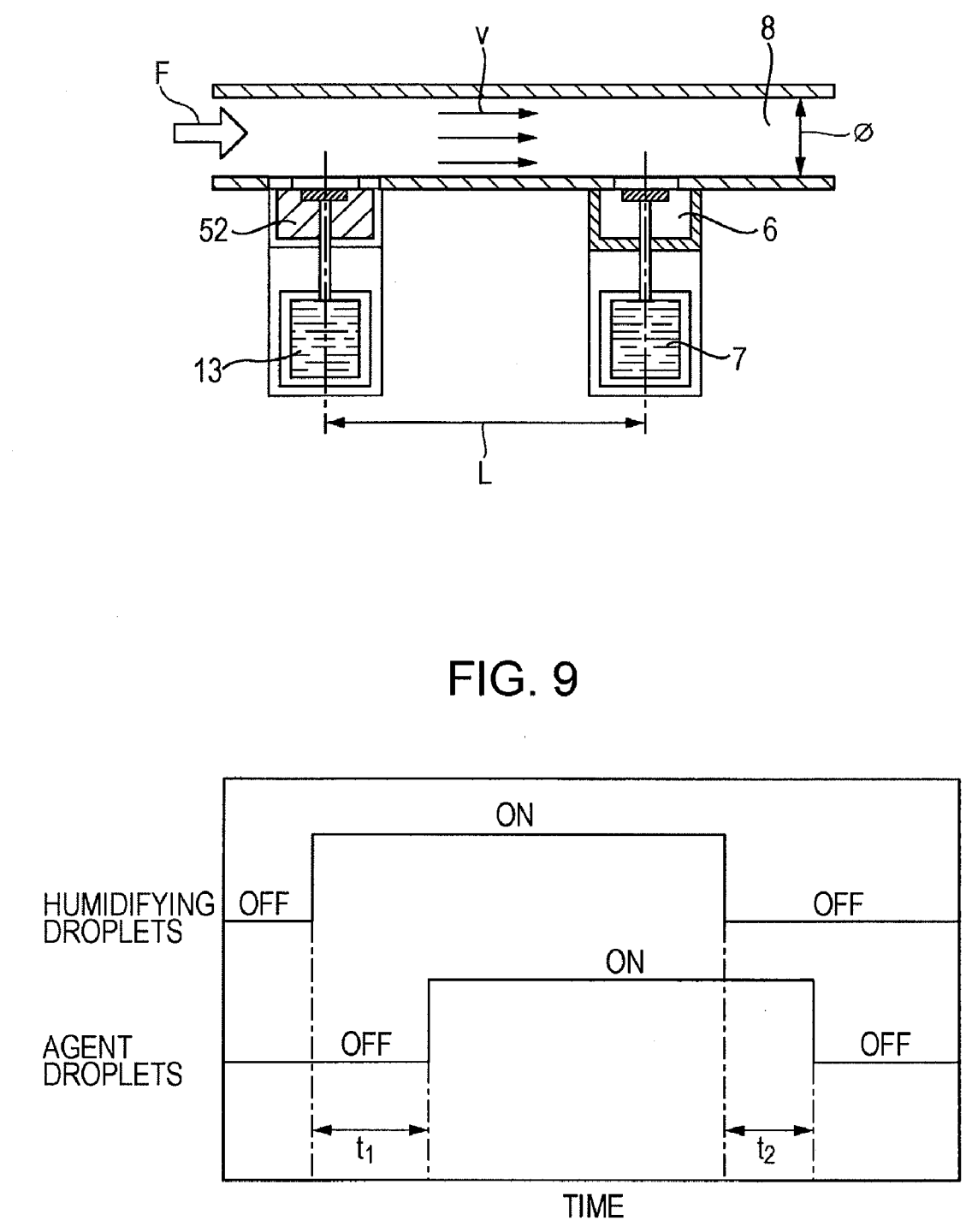

FIGS. 8 and 9 illustrate the timing of discharging humidifying droplets and agent droplets. As shown in FIG. 8, the flow velocity v [m/s] of the airflow can be obtained from the following formula (1):

$$v = \frac{4F}{\pi \phi^2} \quad (1)$$

where F [m³/s] is the volume flow of air taken into the airflow path 8 to bring agent droplets to the user's mouth, and φ [m] is the diameter of the path 8.

The time T [s] until when humidifying droplets reach the place where agent droplets are discharged is obtained from the following formula (2):

$$T = \frac{L}{v} \quad (2)$$

where L [m] is the distance between the humidifying droplet discharge unit 52 and the agent discharge cartridge 6.

FIG. 9 is a timing diagram illustrating a discharge timing of humidifying droplets and agent droplets. In this diagram, "ON" indicates discharge period and "OFF" indicates non-discharge period. In the diagram, $t_1$ is the time from the start of discharge of humidifying droplets to the start of discharge of agent droplets, and $t_2$ is the time from the stoppage of discharge of humidifying droplets to the stoppage of discharge of agent droplets. In order to discharge humidifying droplets and thereby maximize the increase in humidity in the space where an airflow is generated, the time $t_1$ from the start of discharge of humidifying droplets to the start of discharge of agent droplets is larger than the time T until when humidifying droplets reach the place where agent droplets are discharged. The time $t_2$ from the stoppage of discharge of humidifying droplets to the stoppage of discharge of agent droplets is smaller than T. This makes it possible to keep the airflow saturated while agent droplets are discharged and thereby prevent the evaporation of agent droplets.

Sixth Embodiment

Figure 10:
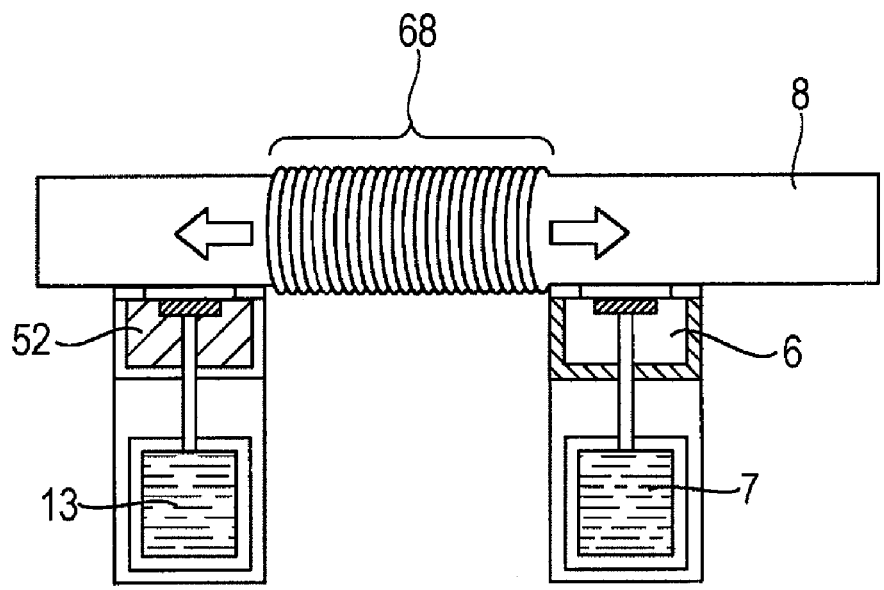

FIG. 10 is a sectional view of an inhalation apparatus according to a sixth embodiment. In order to change the distance between the humidifying droplet discharge unit 52 and the agent discharge cartridge 6 of the fifth embodiment, this embodiment has an accordion structure 68 that elongates and contracts the airflow path 8. By changing the distance between the humidifying droplets discharge unit 52 and the agent discharge cartridge 6, the timing of discharging humidifying droplets can be optimized.

Figure 11:
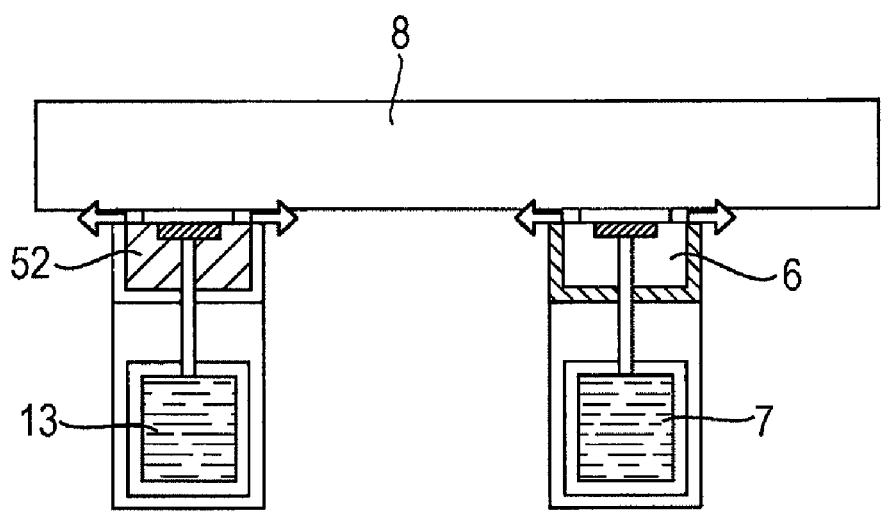

Alternatively, as shown in FIG. 11, by providing a moving mechanism that slides the humidifying droplet discharge unit 52, the agent discharge cartridge 6, or both relative to the airflow path 8, the distance between the humidifying droplet discharge unit 52 and the agent discharge cartridge 6 can be changed.

Seventh Embodiment

Figure 12:
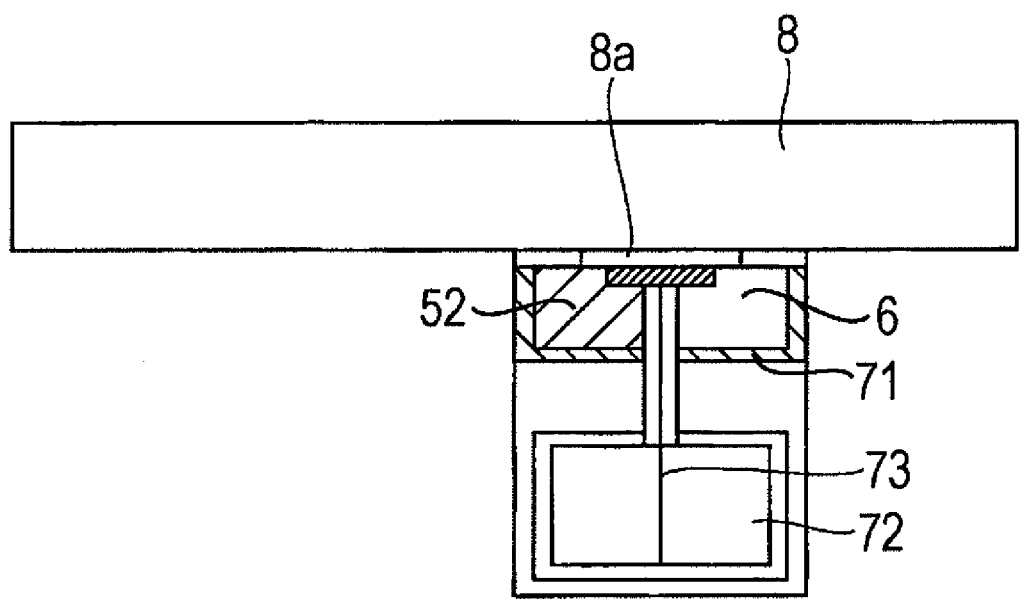

FIG. 12 is a sectional view of an inhalation apparatus according to a seventh embodiment. In this embodiment, a humidifying droplet discharge unit 52 and an agent discharge cartridge 6 are incorporated into the same discharge unit 71. The "discharge unit" is an integrated combination of a tank holding an agent liquid or a humidifying liquid, a discharge head discharging the agent liquid or the humidifying liquid, and a tube supplying the agent liquid or the humidifying liquid from the tank to the discharge head, and does not include other components of an inhalation apparatus such as an airflow path, a control board, and a battery. The tank 72 of the discharge unit 71 is provided with a partition to separately hold the humidifying liquid and the agent liquid. If the diameter of humidifying droplets is smaller than that of agent droplets, the evaporation of agent droplets can be further prevented. The humidifying droplet discharge unit 52 may be located away from an agent intake 8a that also functions as a humidification port.

Figure 13:
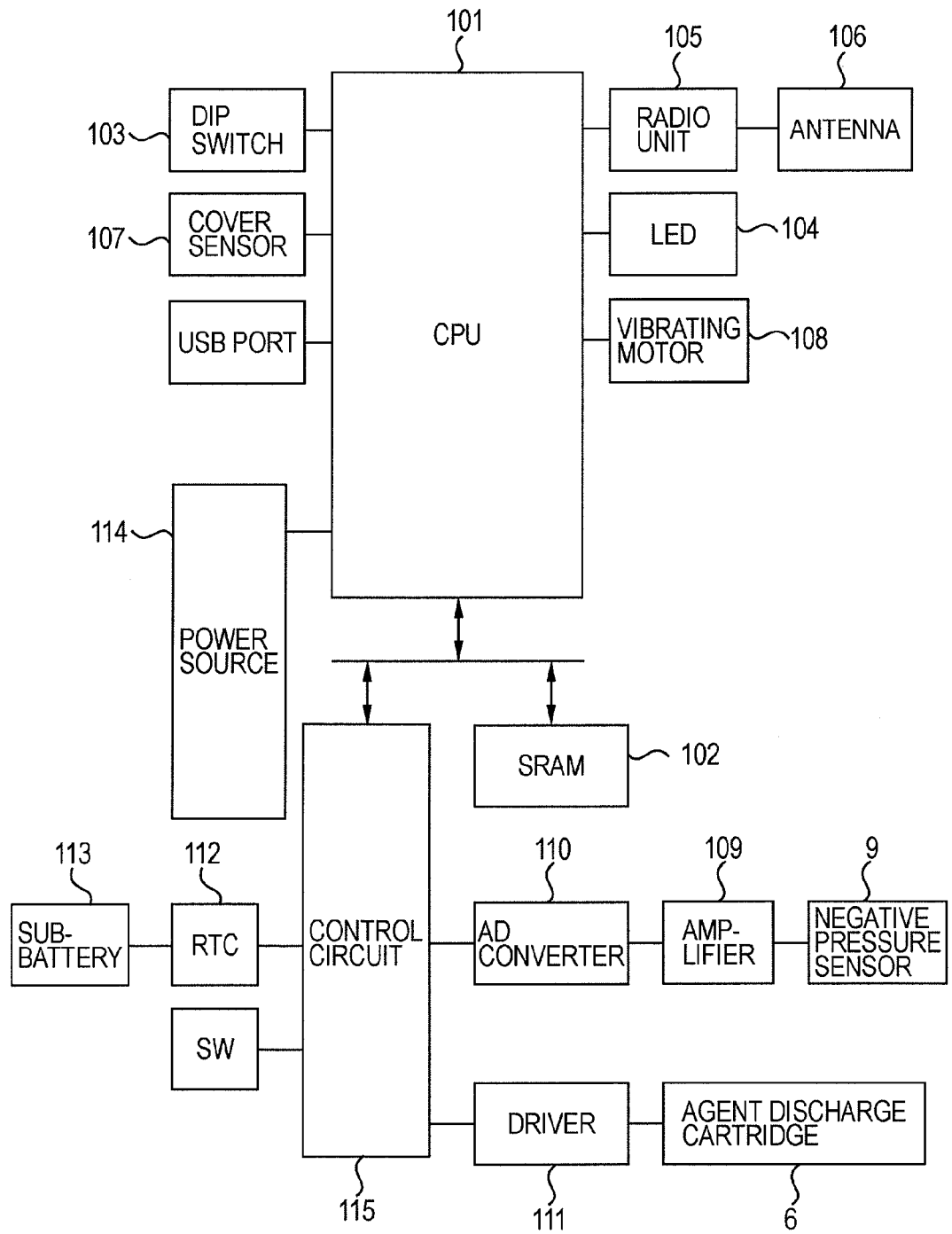

FIG. 13 is a block diagram showing a control system of an inhalation apparatus of the present invention. Reference numeral 101 denotes a CPU, which is an arithmetic processing unit and has a built-in flash ROM storing a program. Reference numeral 102 denotes a SRAM, which is a readable and writable memory for temporarily storing data when the program runs. Reference numeral 103 denotes a DIP switch, which is connected to a port of the CPU 101 and used for setting ON/OFF information and loading the information into the CPU 101. Reference numeral 104 denotes a LED, which is a display device for notifying the user or maintenance worker of the state of the apparatus. Reference numeral 105 denotes a radio unit, which conducts radio communication for transmitting the state of the apparatus and the memory content to a host and receiving data from the host. Reference numeral 106 denotes an antenna for the radio unit. Reference numeral 107 denotes a cover sensor, which detects whether the access cover 2 is open or closed. Reference numeral 108 denotes a vibrating motor. Reference numeral 109 denotes an amplifier, which level-converts and amplifies the output of the pressure sensor 9. Reference numeral 110 denotes an AD converter, which converts the analog output of the amplifier 109 into a digital signal. Reference numeral 111 denotes a driver, which controls the discharge head. Reference numeral 112 denotes a real-time clock (RTC) having a calendar and clock function. Reference numeral 113 denotes a backup battery for the RTC 112. Reference numeral 114 denotes a power source, which makes various voltages supplied to an electric circuit and includes a main battery, a charging circuit, a reset circuit, a power switch, and so forth. Reference numeral 115 denotes a control circuit, which processes signals output from or input into various blocks and is connected with the CPU 101 via a bus.

By operating the power switch, the power source 114 outputs a reset signal to the CPU 101, and the CPU 101 is initialized by the signal. The CPU 101 starts operation by the program stored in the flash ROM and takes in the state of the DIP switch 103. If there is no special setting, the CPU 101 starts operation in a normal operation mode. The output of the pressure sensor 9 changes by inhalation of the user. The change is transmitted to the CPU 101 via the amplifier 109, the AD converter 110, and the control circuit 115. When the inhalation volume exceeds a predetermined threshold, the CPU 101 applies a voltage to the vibrating motor 108 so as to cause the motor to vibrate, and sends a pulse signal to the agent discharge cartridge 6 via the control circuit 115 and the driver 111. In response to the signal, agent droplets are discharged from the discharge head 6a of the agent discharge cartridge 6. After discharging for a prescribed time, the apparatus continues vibrating for a prescribed time to urge the user to inhale.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-283221 filed Oct. 18, 2006, which is hereby incorporated by reference herein in its entirety.

What is claimed is:

1. An inhalation apparatus comprising:
   an airflow path communicating with a suction port through which a user inhales an agent;
   an agent discharger configured to discharge an agent supplied to said airflow path;
   a humidifier located outside said airflow path and configured to humidify an airflow in said airflow path generated by an inhalation by the user;
   a humidification port; and
   a film, placed at the humidification port, that transmits vapor but does not transmit water.

2. The inhalation apparatus according to claim 1, wherein said humidifier is located upstream of said agent discharger in said airflow path.

3. The inhalation apparatus according to claim 1, wherein the cross-sectional area of a part of said airflow path where said humidifier is located is larger than the cross-sectional area of a part of said airflow path where said agent discharger is located.

4. The inhalation apparatus according to claim 1, wherein said humidifier is detachable from said airflow path.

5. The inhalation apparatus according to claim 4, wherein said humidifier is detachable together with a part of said airflow path.

6. The inhalation apparatus according to claim 1, wherein said humidifier includes a humidifying liquid discharger configured to discharge humidifying liquid into said airflow path and a discharge control unit configured to control said humidifying liquid discharger.

7. The inhalation apparatus according to claim 6, wherein the diameter of a discharge port of said humidifying liquid discharger is smaller than the diameter of a discharge port of said agent discharger.

8. The inhalation apparatus according to claim 6, wherein said agent discharger discharges the agent after the airflow humidified by said humidifying liquid discharger reaches the position of said agent discharger in said airflow path, and said agent discharger stops discharging the agent while the humidified airflow exists at the position of said agent discharger in said airflow path.

9. The inhalation apparatus according to claim 6, further comprising a mechanism configured to change the distance between said humidifying liquid discharger and said agent discharger.

10. The inhalation apparatus according to claim 6, wherein said agent discharger and said humidifying liquid discharger are placed in the same discharge unit.

* * * * *